United States Patent [19]
Stellman et al.

[11] Patent Number: 6,091,490
[45] Date of Patent: Jul. 18, 2000

[54] FIBER-OPTIC PIPETTE (FOP) FOR RAPID LONG PATHLENGTH CAPILLARY SPECTROSCOPY

[75] Inventors: Christopher M. Stellman, Waldorf; Frank Bucholtz; Kenneth J. Ewing, both of Crofton, all of Md.

[73] Assignee: The United States of America as represented by the Secretary of the Navy, Washington, D.C.

[21] Appl. No.: 09/126,221

[22] Filed: Jul. 30, 1998

[51] Int. Cl.[7] .............................. G01N 21/01; G01J 3/00
[52] U.S. Cl. ............................................ 356/300; 356/244
[58] Field of Search ..................................... 356/300, 301, 356/303, 319, 326, 311, 244; 385/12, 13, 123, 125, 126, 39

[56] References Cited

U.S. PATENT DOCUMENTS

| | | | |
|---|---|---|---|
| 5,304,492 | 4/1994 | Klinkhammer | 436/52 |
| 5,322,192 | 6/1994 | Godolphin et al. | 222/83 |
| 5,416,879 | 5/1995 | Liu | 385/125 |
| 5,621,522 | 4/1997 | Ewing et al. | 356/301 |
| 5,751,416 | 5/1998 | Singh et al. | 356/311 |

OTHER PUBLICATIONS

Stellman et al.; A Fiber–Optic Pipette for Rapid Long–Pathlength Capillary Spectroscopy; Sensors and Activators B 46, pp. 56–60, 1998.

Primary Examiner—Frank G. Font
Assistant Examiner—Michael P. Stafira
Attorney, Agent, or Firm—Barry A. Edelberg; Charles J. Stockstill

[57] ABSTRACT

The fiber-optic pipette (FOP) couples a glass capillary, common syringe and a single optical fiber together to provide for a facile means of achieving long-pathlength capillary spectroscopy. The FOP acquires rapid spectroscopic measurements of small-volume liquid samples, while simultaneously achieving signal enhancements of the collected spectroscopic signal.

6 Claims, 3 Drawing Sheets

FIBER-OPTIC PIPETTE (FOP) FOR RAPID LONG PATHLENGTH CAPILLARY SPECTROSCOPY

BACKGROUND OF THE INVENTION

1. Field of the Invention

This invention pertains generally to a device for analyzing a sample and more specifically to a device for performing long-pathlength capillary spectroscopy on a sample.

2. Description of the Related Art

Capillary spectroscopy is frequently used in the analysis of small-volume liquid samples. Traditionally, optical spectroscopy of samples in capillary tubes has been achieved by using simple lenses to excite the sample and collect the resulting signal of interest, FIG. 1a. More recently, these standard optical arrangements have been replaced with fiber-optics, FIG. 1b. Coupling of a fiber-optic probe to the end of a capillary tube has provided a much simpler means of sample excitation and signal collection. In addition, this arrangement has allowed for the excited and collected light to be efficiently waveguided throughout the sample medium over a long pathlength. Thus, a larger sample is interrogated (opposed to traditional capillary or non-capillary measurements) and significant signal enhancements have been achieved.

While the advantages of long-pathlength capillary spectroscopy are noteworthy, the technique has often been underutilized due to the expense, complexity and time requirements associated with current technologies. To date, these methods employ two distinct steps. First, the capillary is filled using one of several techniques, and second, the capillary is coupled to a fiber-optic probe for spectroscopic analysis. Disadvantages for each of these steps (in the current form) are as shown below.

The filling of long-pathlength capillaries is typically achieved via pressure delivery systems, mechanical pumps or capillary submersion. Pressure delivery and mechanical pumping can be expensive and require a significant amount of equipment, maintenance and overhead. Capillary submersion is comparatively inexpensive but requires a large amount of sample. This is an option that often does not exist and contradicts the logic of employing capillary spectroscopy in the first place.

After the capillary is filled it is coupled to a fiber probe for spectroscopic analysis. Because considerable alignment is required prior to each run, the time required to sample numerous analytes of interest can become impractical. Furthermore, the optimization of such alignments can vary from one sample to the next, making the comparison of a series of measurements difficult. Such alignment problems can be avoided by permanently coupling the probe and capillary, however, it becomes difficult to flush the system between samples. This can result in residual contaminants being left behind and can adversely effect the results of subsequent measurements.

SUMMARY OF THE INVENTION

An objective of this invention is to provide a simple means of performing long-pathlength capillary spectroscopy.

Another objective of this invention is to make it possible to acquire rapid spectroscopic measurements of small-volume liquid samples while simultaneously achieving signal enhancements of the collected spectroscopic signal.

These and other objectives are accomplished by the fiber-optic pipette (FOP) which couples a glass capillary, common syringe and a single optical fiber together to provide for a facile means of achieving long-pathlength capillary spectroscopy. The FOP acquires rapid spectroscopic measurements of small-volume liquid samples, while simultaneously achieving signal enhancements of the collected spectroscopic signal.

DESCRIPTION OF THE PREFERRED EMBODIMENT

Figure 1A:
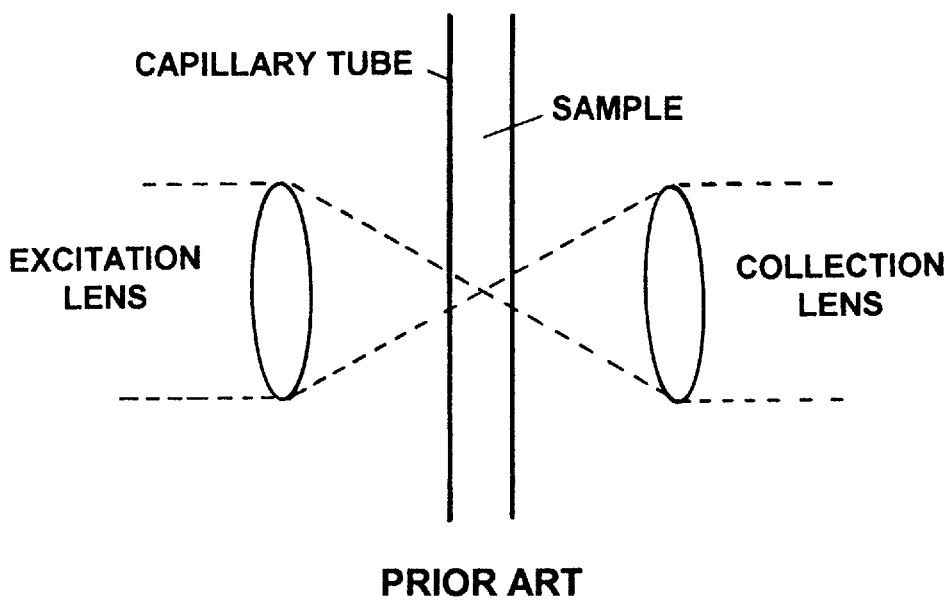
FIG. 1a shows a standard optical arrangement for optical spectroscopy of samples in capillary tubes using simple lenses to excite the sample and collect the resulting signal of interest.
Figure 1B:
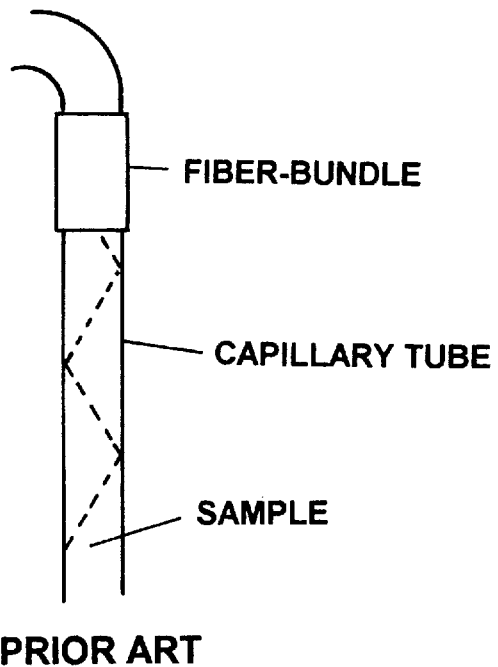
FIG. 1b shows a standard optical arrangement or optical spectroscopy for samples utilizing fiber-optics.
Figures 2, 3:
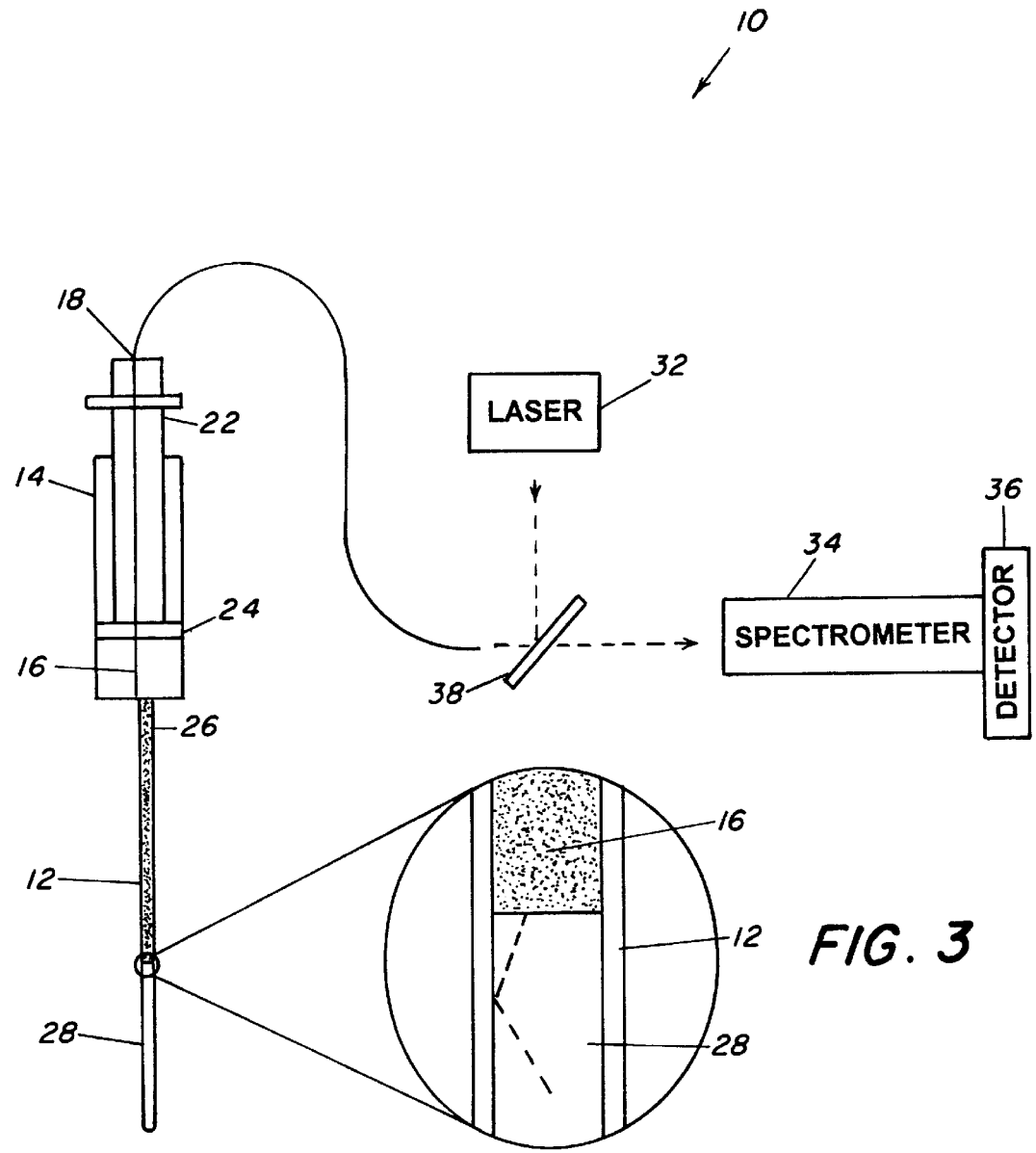
FIG. 2 shows the arrangement of a fiber-optic pipette (FOP) for long pathlength capillary spectroscopy.
FIG. 3 shows the area of the FOP where the optical-fiber interfaces with the sample.

A fiber-optic pipette (FOP) 10 for long pathlength capillary spectroscopy, as shown in FIG. 2, uniquely couples a glass capillary 12, a common syringe 14, and a single optical fiber 16 to provide for a facile means of achieving long-pathlength capillary spectroscopy. The FOP 10 consists of a common 10 mL plastic syringe 14 that is directly coupled to a glass capillary tube 12. Preferably, the syringe is a type 16033-10cc manufactured by Becton Dickinson of Rutherford, N.J., however any other type of syringe may be used. The syringe 14 is modified to allow a 250 $\mu$m-core optical fiber 16 to be passed through the center 18 of the syringe 14 while maintaining an air-tight seal. The optical fiber 16 is threaded through two small holes (not shown) drilled in the syringe handle 22 and diaphragm 24, and then is fed directly into the center of a 1 mm inner diameter capillary 12. Preferably, the optical fiber is a type HCGMO 100r manufactured by HCS Fiber Optic Products of Avon, Conn., however, and any similar type optical fiber may be used. The 10 cm long capillary 12 is attached to the end of the syringe 14 via a needle mount 26 and is held in place by a press fit. The capilary is preferably glass, however, any type may be used. The external diameter of the optical fiber 16 closely matches that of the capillary 12 inner diameter to insure a tight seal.

A sample 28 is collected by placing the capillary 12 into a reservoir of interest (not shown) and retracting the syringe handle 22. The handle 22 pulls back the optical fiber 16 while simultaneously drawing the sample 28 into the capillary 12. By pulling the fiber 16 to the top of the capillary 12 a long-pathlength sampling arrangement is created and a spectroscopic measurement can be made.

Excitation of the sample and collection of the signal of interest are achieved with a single optical fiber 16. The excitation source consists of, but is not limited to, a laser 32, preferably an argon ion laser, type Innova 70 manufactured by Coherent of Santa Clara, Calif. The resulting signal is dispersed via an appropriate wavelength selection device (e.g., a spectometer 34) and collected via an appropriate detector 36, preferably, but not limited to, a SPEX (CCD) model 270M manufactured by Instruments S.A. of Edison, N.J. A beamsplitter 38 is employed at the end of the fiber 16 to wavelength discriminate between the excitation and resulting signal.

Figure 4:
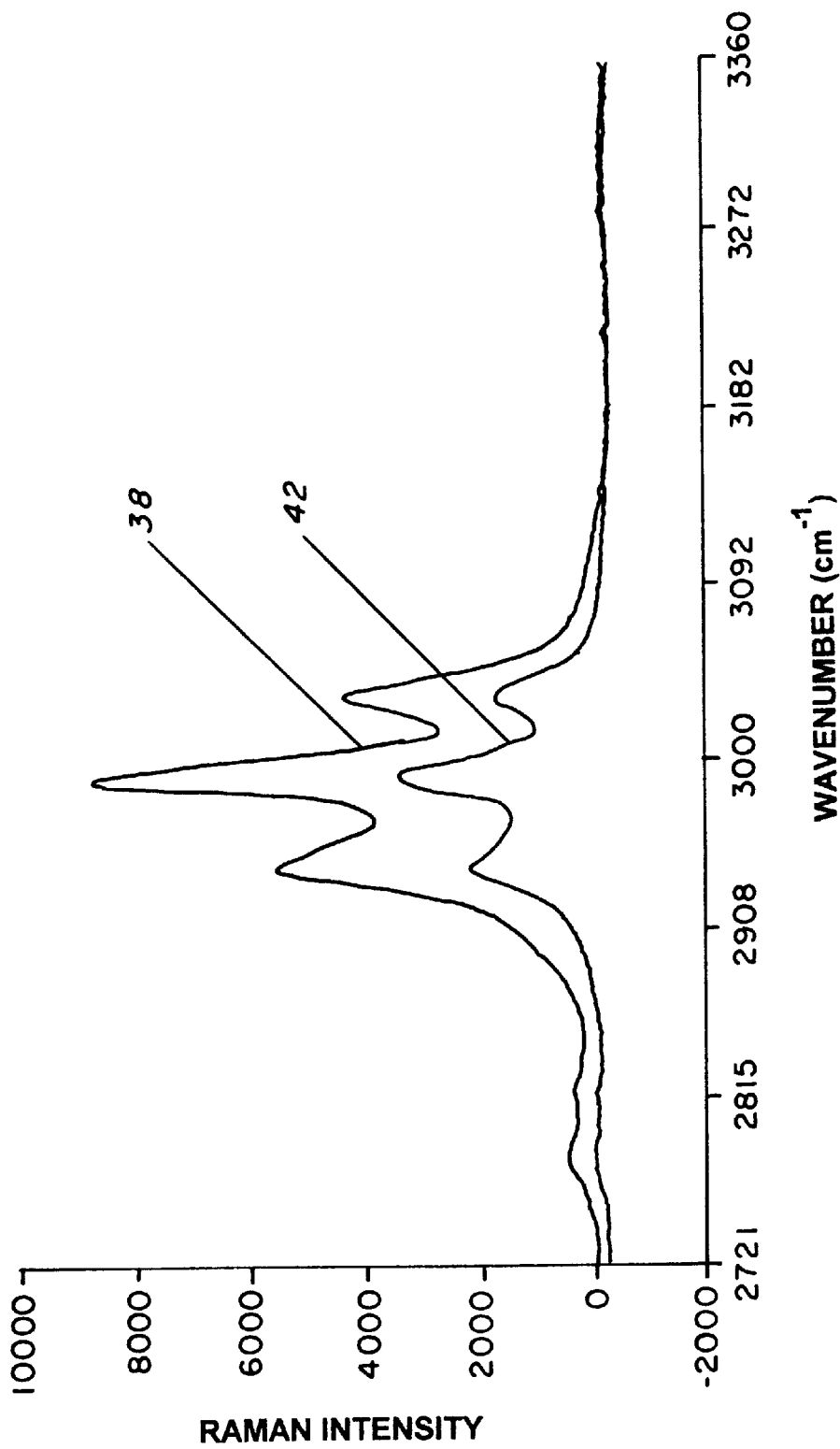
FIG. 4 shows the Raman spectrum of ethanol collected with and without the FOP.

For demonstration purposes, the device has been used to collect the Raman spectrum of neat ethanol. FIG. 4 shows the Raman spectrum of ethanol collected with 38 and without 42 the FOP 10. The non-FOP spectrum 42 did not employ a capillary and was collected by simply dipping the optical fiber into a standard 100 ml beaker of ethanol. In both cases a single fiber was employed and all other equipment and experimental parameters were the same. From FIG. 4 it is evident that a Raman spectrum can be collected using the FOP. Furthermore, it is demonstrated that the FOP achieves the expected long pathlength signal enhancement. The signal-to-noise ratio of the Raman spectrum acquired using the pipette to that acquired not using the pipette is better by a factor of 2.6.

Several advantages are associated with the FOP 10. These advantages are largely the result of the FOP's 10 novel integration of liquid sampling and spectroscopic interrogation. Again referring to FIG. 2, this integration consists of a simple syringe 14, long-pathlength capillary 12, and single fiber-optic 16, that when used in conjunction, serve as both a unique sampling mechanism as well as an efficient spectroscopic probe.

Because the FOP 10 is an integrated system and no alignment is required between liquid sampling and spectroscopic interrogation it allows for rapid measurements to be taken. A sample can be drawn into the capillary 12 in less than two seconds and the time required for subsequent spectral analysis is only limited by the strength of the signal of interest. This rapid measurement capability allows for the practical analysis of numerous samples over a short period of time.

Another advantage of the FOP 10 is it's ability to make measurements in small places. The FOP's 10 small profile allows it to be placed into many hard to reach reservoirs (e.g., small-mouth storage vials, test tubes, distillation apparatuses, etc.). Furthermore, these measurements can be achieved with very small quantities of sample 28. For example, the use of a 1 cm long capillary would require a sample 28 volume of only 7.85 $\mu$L.

The FOP 10 is also advantageous in that it is dependent on inexpensive glass capillaries for sampling. While a single capillary can be used for numerous samples of interest, it can also be disposed of after each analysis. This offers the user a simple means of avoiding cross contamination of analytes.

Versatility is also a strong advantage of the FOP 10. As previously noted, the FOP 10 is compatible with, but in no way limited to Raman spectroscopy. Virtually all spectroscopic methods capable of utilizing a standard backscattering collection geometry are compatible. This includes such spectroscopies as Rayleigh scattering, fluorescence, phosphorescence, chemiluminescence and infrared reflection.

The FOP 10 is also versatile in it's ability to be used with varying capillary 12 sizes. it is possible to increase signal enhancements by simply lengthening the capillary 12. Likewise, the required sample 28 volume can be lowered by decreasing the capillary's 12 inner diameter. Because optical fibers 16 are available in many sizes such changes are simple to achieve, only requiring that the internal capillary 12 diameters and external fiber 16 diameter be closely matched.

Because the FOP 10 relies on a simple plastic syringe 14, inexpensive glass capillaries 12 and silica-based fibers 16 it is an economical device. No expensive pumps or pressure delivery systems are required and the use of expensive and/or complex optics can be avoided.

Because the FOP 10 provides a rapid means of performing long-pathlength capillary spectroscopy on small-volume liquid samples it is conducive to a plethora of commercial, research and military applications. In biomedicine, biochemistry and forensics the FOP 10 may be used to sample and spectrometrically interrogate bodily fluids (e.g., blood, saliva, urine, etc.). This would aid in blood-typing, drug and steroid screening, and the determination of carbohydrate and/or lipid levels. In organic and inorganic chemistry the FOP 10 may be used to characterize synthetic molecules that are only available in small quantities. The FOP 10 may also be used for quality control testing during bulk production of the synthetic materials. In the field of environmental chemistry, the FOP 10 may be used to characterize ground and surface waters, municipal waste discharges, atmospheric fallout, and accidental and intentional spills. In military applications, the FOP 10 may be used to characterize ship bilge waters, determine fuel and/or oil quality, and screen for chemical warfare byproducts.

Although this invention has been described in relation to an exemplary embodiment thereof, it will be understood by those skilled in the art that still other variations and modifications can be affected in the preferred embodiment without detracting from the scope and spirit of the invention as described in the claims.

What is claimed is:

1. A device for performing long-pathlength capillary spectroscopy comprised of:
    a syringe having a handle, a diaphragm and a needle mount;
    a single optical fiber providing a facile means of achieving long-pathlength capillary spectroscopy;
    a capillary tube connected to the needle mount;
    said optical fiber extending through a hole in the syringe handle, diaphragm and needle mount into the capillary tube;
    means for transmitting an excitation signal through the optical fiber onto the sample which produces a resulting signal;
    means for discriminating between the excitation and resulting signal passing through the optical fiber; and
    means of achieving long-pathlength capillary spectroscopy of the resulting signal.

2. A device, as in claim 1, wherein the means for transmitting an excitation signal through the optical fiber onto the sample which produces a resulting signal is an optical light source.

3. A device, as in claim 2, wherein the optical light source is an optical laser.

4. A device, as in claim 1, wherein the means for discriminating between the excitation and resulting signal passing through the optical fiber is an optical beamsplitter.

5. A device, as in claim 1, wherein the means of achieving long-pathlength capillary spectroscopy of the resulting signal is a spectrometer.

6. A method for performing long-pathlength capillary spectroscopy comprised of the steps of:
    Placing a syringe having an optical fiber extending through the center of the syringes handle, diaphragm, needle mount and capillary tube into a sample to be analyzed;
    transmitting an optical light onto the sample through the optical fiber; and
    transmitting a reflected light from the sample to a spectrometer through the optical fiber where long-pathlength capillary spectroscopy is performed by a spectrometer.

* * * * *